(12) United States Patent
Takata

(10) Patent No.: US 7,309,143 B2
(45) Date of Patent: Dec. 18, 2007

(54) OPTICAL MATERIAL, OPTICAL ELEMENT, ILLUMINATOR AND DISPLAY DEVICE

(75) Inventor: Yoshiki Takata, Suzuka (JP)

(73) Assignee: Sharp Kabushiki Kaisha, Kyoto (JP)

( * ) Notice: Subject to any disclaimer, the term of this patent is extended or adjusted under 35 U.S.C. 154(b) by 419 days.

(21) Appl. No.: 11/012,738

(22) Filed: Dec. 15, 2004

(65) Prior Publication Data

US 2005/0135118 A1    Jun. 23, 2005

(30) Foreign Application Priority Data

Dec. 19, 2003 (JP) ............... 2003-421825
Nov. 8, 2004 (JP) ............... 2004-323857

(51) Int. Cl.
*F21V 5/00* (2006.01)

(52) U.S. Cl. ............... 362/246; 362/606; 362/355; 359/599; 252/582; 349/64

(58) Field of Classification Search .......... 362/614, 362/225
See application file for complete search history.

(56) References Cited

U.S. PATENT DOCUMENTS

| | | | |
|---|---|---|---|
| 5,235,497 A |   | 8/1993 | Costa |
| 5,434,762 A |   | 7/1995 | Shemitz |
| 6,050,704 A | * | 4/2000 | Park .................. 362/260 |
| 6,654,088 B2 |   | 11/2003 | Morishita et al. |
| 6,741,307 B2 | * | 5/2004 | Matsunaga et al. ........ 349/112 |
| 6,778,235 B2 | * | 8/2004 | Takahashi et al. ........ 349/65 |
| 6,798,150 B2 |   | 9/2004 | Moon |
| 6,857,759 B2 |   | 2/2005 | Lee et al. |
| 6,939,020 B2 |   | 9/2005 | Lim |
| 7,106,394 B2 |   | 9/2006 | Ono et al. |
| 2003/0026085 A1 |   | 2/2003 | Ueda et al. |
| 2003/0035283 A1 |   | 2/2003 | Lim |
| 2003/0210222 A1 |   | 11/2003 | Ogiwara et al. |
| 2003/0218877 A1 | * | 11/2003 | Moon ............ 362/225 |
| 2004/0012971 A1 | * | 1/2004 | Tsai et al. ............ 362/390 |
| 2004/0070965 A1 |   | 4/2004 | Lin |
| 2004/0119418 A1 |   | 6/2004 | Moon |
| 2004/0140773 A1 |   | 7/2004 | Moon |
| 2004/0189892 A1 |   | 9/2004 | Ono et al. |
| 2005/0024867 A1 |   | 2/2005 | Witham et al. |

FOREIGN PATENT DOCUMENTS

| | | |
|---|---|---|
| JP | 03-259177 | 11/1991 |
| JP | 04-143725 A | 5/1992 |
| JP | 04-172319 | 6/1992 |
| JP | 05-257002 | 10/1993 |
| JP | 6-67176 | 3/1994 |

(Continued)

OTHER PUBLICATIONS

Yoshiki Takata, "Illuminator and Display Device Using the Same", U.S. Appl. No. 11/002,154, filed Dec. 1, 2004.

(Continued)

*Primary Examiner*—Laura Tso
(74) *Attorney, Agent, or Firm*—Keating & Bennett, LLP

(57) ABSTRACT

An optical material of the present invention includes a resin having a luminous transmittance of about 70% or more and a filler mixed therein having a thermal conductivity of about 3 W/m·K or more.

27 Claims, 12 Drawing Sheets

FOREIGN PATENT DOCUMENTS

| | | |
|---|---|---|
| JP | 8-194650 | 7/1996 |
| JP | 09-281339 A | 10/1997 |
| JP | 10-067828 A | 3/1998 |
| JP | 10-143089 | 5/1998 |
| JP | 10-186328 | 7/1998 |
| JP | 2000-310776 | 11/2000 |
| JP | 2001-174813 | 6/2001 |
| JP | 2001-210126 | 8/2001 |
| JP | 2002-122863 | 4/2002 |
| JP | 2003-31003 | 1/2003 |
| JP | 2003-84277 | 3/2003 |
| JP | 2003-215585 | 7/2003 |
| JP | 2003-233071 | 8/2003 |
| JP | 2004-296298 A | 10/2004 |

OTHER PUBLICATIONS

Yoshiki Takata, "Illumination Device and Display Apparatus Including the Same", U.S. Appl. No. 10/977,827, filed Oct. 29, 2004.

Official Communication issued in corresponding Chinese Patent Application No. 2004101013768, dated Feb. 24, 2006.

Official Communication issued in corresponding Taiwanese Patent Application No. 093139400, issued Apr. 10, 2006.

Official Communication issued in corresponding Japanese Patent Application No. 2004-323857, mailed Oct. 17, 2006.

Official communication issued in the counterpart Japanese Application No. 2003-388205, mailed on Apr. 17, 2007.

* cited by examiner

OPTICAL MATERIAL, OPTICAL ELEMENT, ILLUMINATOR AND DISPLAY DEVICE

FIELD OF THE INVENTION

The present invention relates to an optical material, and more particularly, the present invention relates to a resin-containing optical material. The present invention also relates to an optical element made of a resin-containing optical material, and an illuminator and a display device including such an optical element.

BACKGROUND OF THE INVENTION

Liquid crystal display devices are widely used in OA (office automation) equipment, car televisions, monitors for camcorders, etc., for their advantageous features such as light weight, thin structure and small power consumption. Unlike self-luminous display devices such as CRTs, PDPs (plasma display panels) and EL (electroluminescence) devices, liquid crystal display devices use a liquid crystal display element that itself does not produce light. Therefore, in a transmission type liquid crystal display device, a planar illuminator called a "backlight" is provided on the back side of the liquid crystal display element, and the liquid crystal display element controls the amount of output light from the backlight to be transmitted therethrough in each pixel so as to display an image.

Backlights are generally classified into "direct-type" backlights including a plurality of rod-shaped light sources, such as fluorescent tubes, placed directly under a liquid crystal display element, and "edge light-type" backlights including a light source placed along an edge of a lightguide plate so that light from the light source is guided through the lightguide plate to a liquid crystal display element.

A typical structure of a direct-type backlight is illustrated in FIG. 21. A backlight 40 illustrated in FIG. 21 is provided on the back side of a transmission type liquid crystal display panel 48, and includes a plurality of light sources (fluorescent tubes) 41 arranged at regular intervals, a case 42 accommodating the light sources 41, and a diffusion plate 43 provided between the light sources 41 and the liquid crystal display panel 48. The diffusion plate 43 diffuses light output from the light source 41 to increase the uniformity of the output light. The diffusion plate 43 is typically made of a material including a resin and particles dispersed in the resin and having a different refractive index from that of the resin. Because of the difference between the refractive index of the resin matrix and that of the particles dispersed therein, a light-diffusing property is exhibited. An acrylic resin is often used as the resin because it is highly transparent and is easy to mold, and silica beads are often used as the particles because they are highly transparent.

In recent years, since a liquid crystal display device is required to have a very high brightness, the number of the light sources 41 used is increasing, and the amount of heat generated from the light sources 41 is also increasing. However, the diffusion plate 43 is made of a material containing a resin with a low thermal conductivity (for example, acrylic resin has a very low thermal conductivity), and has a low heat-radiating property. Therefore, if a large number of light sources 41 are provided, heat radiation of the diffusion plate 43 may be insufficient, and the temperature distribution across the diffusion plate 43 may become non-uniform, whereby the temperature distribution across the display plane of the liquid crystal display panel 48 may also become non-uniform. Since the optical and electrical characteristics of a liquid crystal material sealed in the liquid crystal display panel 48 are temperature-dependent, a non-uniform temperature distribution across the liquid crystal display panel 48 causes a brightness non-uniformity, and the like, thereby lowering the display quality. Moreover, an excessively high temperature inside the backlight 40 leads to other problems such as a decrease in the luminous efficiency of the light sources 41 and softening of resin-made components. Moreover, as the thickness of a backlight is decreasing recently, the distance between the light source 41 and the diffusion plate 43 is decreasing, whereby such problems are more likely to occur.

In view of this, Japanese Laid-Open Patent Publication No. 4-172319 discloses a method in which a diffusion plate of a backlight is made of a resin material mixed with minute glass particles, thereby improving the heat-radiating property of the diffusion plate.

However, in-depth research by the present inventor revealed that a heat-radiating property that is sufficient in practice cannot be obtained by forming a diffusion plate using a resin material mixed with minute glass particles as disclosed in Japanese Laid-Open Patent Publication No. 4-172319.

These problems occur not only with direct-type backlights but also with edge light-type backlights due to the heat-radiating property of the lightguide plate (lightguide) being insufficient.

SUMMARY OF THE INVENTION

In order to overcome the problems described above, preferred embodiments of the present invention provide an optical material having a desirable heat-radiating property, an optical element made of such an optical material, and an illuminator and a display device including such an optical element.

An optical material according to a preferred embodiment of the present invention includes a resin having a luminous transmittance of about 70% or more, and a filler mixed therein having a thermal conductivity of about 3 W/m·K or more.

In a preferred embodiment, a thermal conductivity of the filler is preferably about 10 W/m·K or more.

In a preferred embodiment, the filler is made of alumina.

In a preferred embodiment, the filler is made of magnesium oxide.

In a preferred embodiment, a luminous transmittance of the resin is preferably about 80% or more.

In a preferred embodiment, the resin is polycarbonate.

In a preferred embodiment, a luminous transmittance of the resin is preferably about 90% or more.

In a preferred embodiment, the resin is an acrylic resin.

In a preferred embodiment, the resin is polystyrene.

In a preferred embodiment, the resin is a methyl methacrylate-styrene copolymer resin.

In a preferred embodiment, the filler is particulate.

In a preferred embodiment, an average particle diameter of the filler is preferably about 1 μm or more.

In a preferred embodiment, a refractive index of the resin is different from that of the filler, thereby realizing a light-diffusing property.

An inventive optical element includes the optical material according to a preferred embodiment described above.

An inventive diffusion plate includes the optical material according to a preferred embodiment described above.

In a preferred embodiment, a haze value of the diffusion plate is preferably about 95% or more.

An illuminator according to another preferred embodiment of the present invention includes a light source, and the diffusion plate as set forth above for diffusing light output from the light source.

An inventive lightguide includes the optical material according to a preferred embodiment described above.

Another inventive illuminator includes a light source, and the lightguide according to a preferred embodiment described above for guiding light output from the light source in a predetermined direction.

According to another preferred embodiment of the present invention, a light-scattering member for scattering light includes the optical material according to a preferred embodiment described above.

Still another preferred embodiment of the present invention provides an illuminator for a display device provided on a back side of a display panel, including a plurality of rod-shaped light sources arranged generally parallel to one another, and the light-scattering member according to a preferred embodiment described above is disposed between two adjacent ones of the plurality of rod-shaped light sources.

In a preferred embodiment, the light-scattering member is located generally in between the two rod-shaped light sources.

In a preferred embodiment, the light-scattering member is a rod-shaped member.

In a preferred embodiment, the light-scattering member is arranged generally parallel to the plurality of rod-shaped light sources.

In a preferred embodiment, a central axis of the light-scattering member is arranged substantially coplanar with central axes of the plurality of rod-shaped light sources.

In a preferred embodiment, the light-scattering member has generally the same outer diameter as that of the plurality of rod-shaped light sources.

In a preferred embodiment, a shape of a cross section of the light-scattering member taken in a direction perpendicular to a longitudinal direction is generally the same as that of each of the plurality of rod-shaped light sources.

In a preferred embodiment, a shape of a cross section of the light-scattering member taken in a direction perpendicular to a longitudinal direction is generally circular.

In a preferred embodiment, the plurality of rod-shaped light sources are each a fluorescent tube.

Still another preferred embodiment of the present invention provides an illuminator for a display device provided on a back side of a display panel, and includes at least one light source including a plurality of rod-shaped portions arranged generally parallel to one another, and a bent portion connecting two adjacent ones of the plurality of rod-shaped portions to each other, and the light-scattering member according to a preferred embodiment described above disposed between two adjacent ones of the plurality of rod-shaped portions.

In a preferred embodiment, the light-scattering member is located generally in between the two rod-shaped portions.

In a preferred embodiment, the light-scattering member is a rod-shaped member.

In a preferred embodiment, the light-scattering member is arranged generally parallel to the plurality of rod-shaped portions.

In a preferred embodiment, a central axis of the light-scattering member is arranged substantially coplanar with central axes of the plurality of rod-shaped portions.

In a preferred embodiment, the light-scattering member has generally the same outer diameter as that of the plurality of rod-shaped portions.

In a preferred embodiment, a shape of a cross section of the light-scattering member taken in a direction perpendicular to a longitudinal direction is generally the same as that of each of the plurality of rod-shaped portions.

In a preferred embodiment, a shape of a cross section of the light-scattering member taken in a direction perpendicular to a longitudinal direction is generally circular.

In a preferred embodiment, the at least one light source is at least one fluorescent tube.

Another preferred embodiment of the present invention provides a light source holder for an illuminator, including the optical material according to a preferred embodiment described above.

Still another preferred embodiment of the present invention is an illuminator including a light source and the light source holder according to a preferred embodiment described above for holding the light source.

Another preferred embodiment of the present invention provides a display device including the illuminator according to a preferred embodiment described above, and a display panel for displaying an image by using light output from the illuminator.

The optical material of various preferred embodiments of the present invention preferably includes a resin having a luminous transmittance of about 70% or more, and a filler mixed therein having a thermal conductivity of about 3 W/m·K or more, thereby providing a preferable optical characteristic (transparency) and a desirable heat-radiating property.

Other features, elements, characteristics and advantages of the present invention will become more apparent from the following detailed description of preferred embodiments thereof with reference to the attached drawings.

DETAILED DESCRIPTION OF THE PREFERRED EMBODIMENTS

Preferred embodiments of the present invention will now be described with reference to the drawings. Note that the present invention is not limited to the following preferred embodiments.

Preferred Embodiment 1

Figure 1:
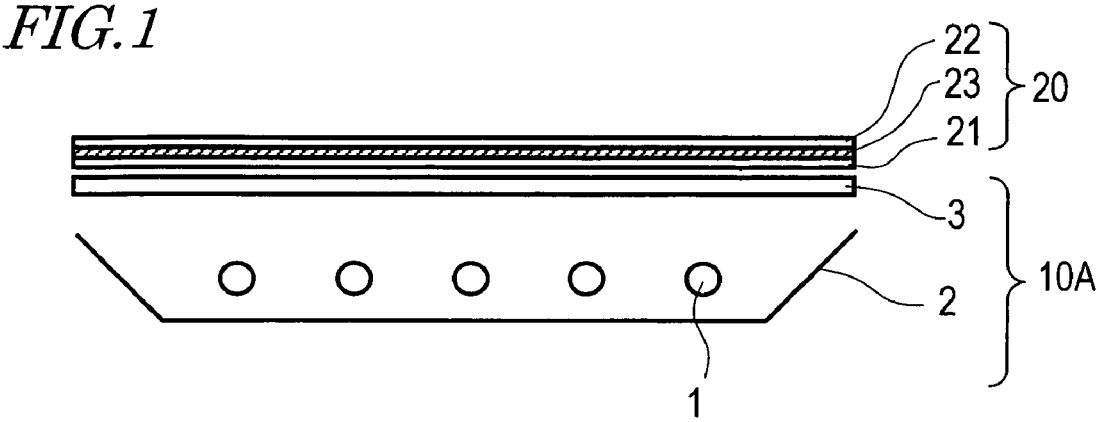
FIG. 1 is a cross-sectional view schematically illustrating an illuminator 10A according to a preferred embodiment of the present invention.

Referring to FIG. 1, an illuminator 10A of the present preferred embodiment will now be described.

The illuminator 10A is a so-called "backlight" provided on the back side (the side away from the viewer) of a liquid crystal display panel 20, as illustrated in FIG. 1. The liquid crystal display panel 20 includes a pair of substrates (e.g., glass substrates) 21 and 22 and a liquid crystal layer 23 provided therebetween, and modulates light output from the illuminator 10A to display an image. The liquid crystal display panel 20 includes a region in each pixel in which an image is displayed in a transmission mode. Thus, the liquid crystal display panel 20 is a transmission type or transmission-reflection type liquid crystal display panel.

The illuminator 10A is a direct-type backlight, and includes a plurality of rod-shaped light sources 1 arranged generally parallel to one another. In the present preferred embodiment, the rod-shaped light sources 1 are cold cathode fluorescent tubes (CCFTs). The rod-shaped light sources 1 are held in a case 2 by supporting members (holders, not shown) provided in the case 2, and a diffusion plate 3 is provided between the rod-shaped light sources 1 and the liquid crystal display panel 20. The diffusion plate 3 diffuses light output from the light sources 1 and thereby improves the uniformity of the output light. Typically, in order to increase the light efficiency, the surface of the case 2 that is closer to the rod-shaped light sources 1 is provided with a highly-reflective member (e.g., a light-reflecting sheet), or the case 2 itself is made of a highly-reflective material.

Figure 2:
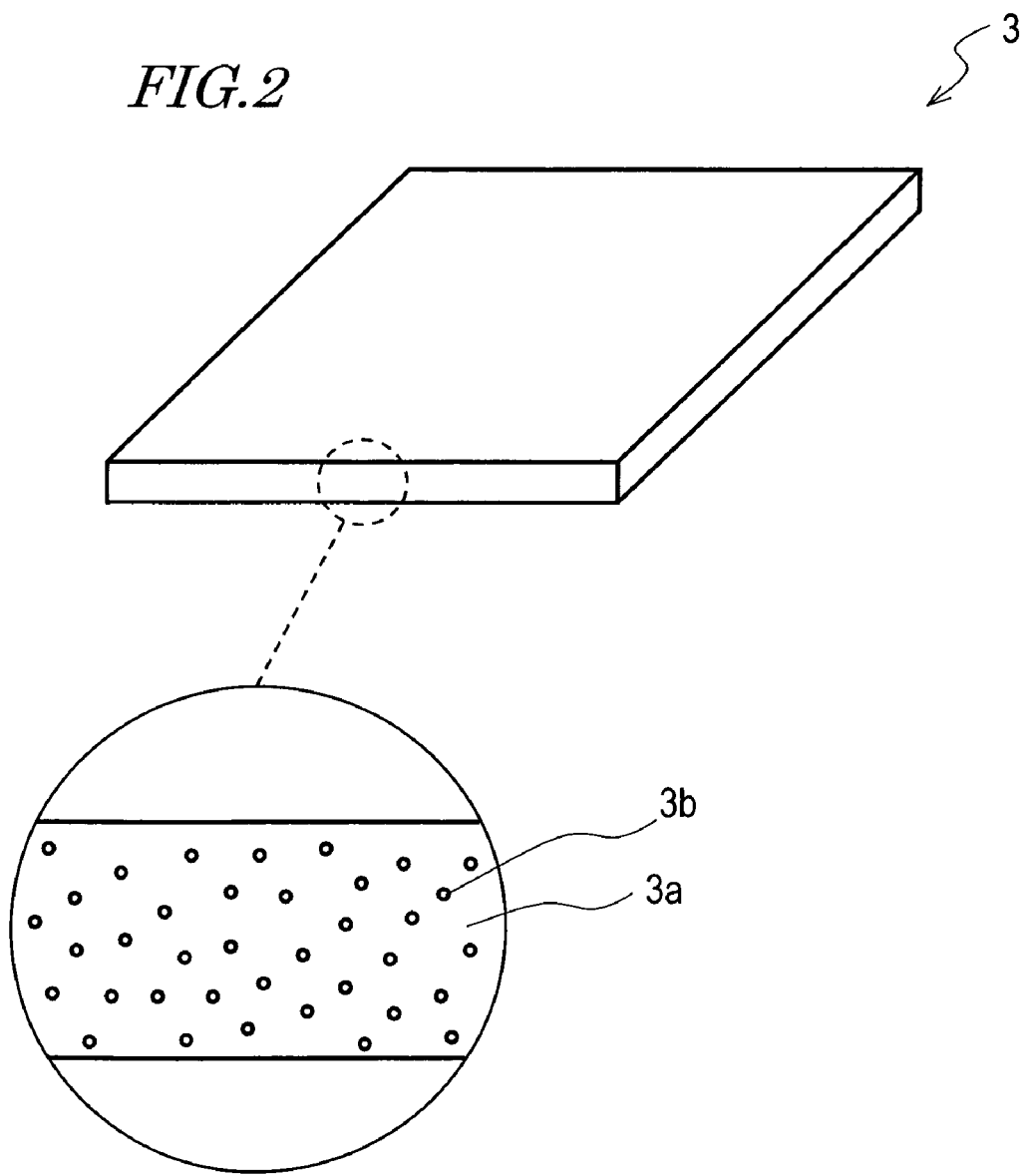
FIG. 2 schematically illustrates a diffusion plate 3 provided in the illuminator 10A according to a preferred embodiment of the present invention.

The illuminator 10A of the present preferred embodiment preferably has substantially the same structure as that of a known direct-type backlight except that the diffusion plate 3 is made of an optical material different from those used conventionally. Referring to FIG. 2, the diffusion plate 3 of the illuminator 10A will now be described.

The diffusion plate 3 preferably includes a resin matrix 3a, and a filler (inorganic filler) 3b dispersed in the resin matrix 3a, as illustrated in FIG. 2. The filler 3b used in the present preferred embodiment is preferably particulate, but other fillers may be used. The refractive index of the filler 3b is different from that of the resin matrix 3a, whereby the diffusion plate 3 exhibits a light-diffusing property.

The diffusion plate 3 is preferably made of an optical material including a resin having a luminous transmittance of about 70% or more and a filler mixed therein having a thermal conductivity of about 3 W/m·K or more. As a result, the diffusion plate 3 has a preferable optical characteristic as an optical element while having a desirable heat-radiating property. This will now be described in greater detail.

First, the reason why a preferable optical characteristic is obtained with luminous transmittance having a value of about 70% will be explained. The luminous transmittance $T(\%)$ can be expressed as $T=(T_1/T_0)\times 100$, wherein $T_0$ is the intensity of incident light and $T_1$ is the intensity of all transmitted light for visible light (wavelength: 350 nm to 800 nm). The luminous transmittance is measured in accordance with ASTM D1003 by using, for example, HR-100 manufactured by Murakami Color Research Laboratory. The luminous transmittance of a resin used in an optical material is typically measured with a test piece having a thickness of about 3 mm. Accordingly, the "luminous transmittance" of a resin as used herein refers to a "luminous transmittance measured with a 3 mm thick test piece", unless otherwise specified.

In a common direct-type backlight, light sources such as CCFTs are often arranged at a pitch of about 20 mm. Therefore, in order to eliminate the image of the light sources arranged at such a pitch (i.e., to eliminate the difference between the brightness in areas directly above the light sources and that in other areas between light sources), the diffusion plate is required to have an optical distance of about 20 mm or more. Thus, the resin matrix of the diffusion plate needs to transmit a sufficient amount of light for an optical distance of about 20 mm.

Figure 3:
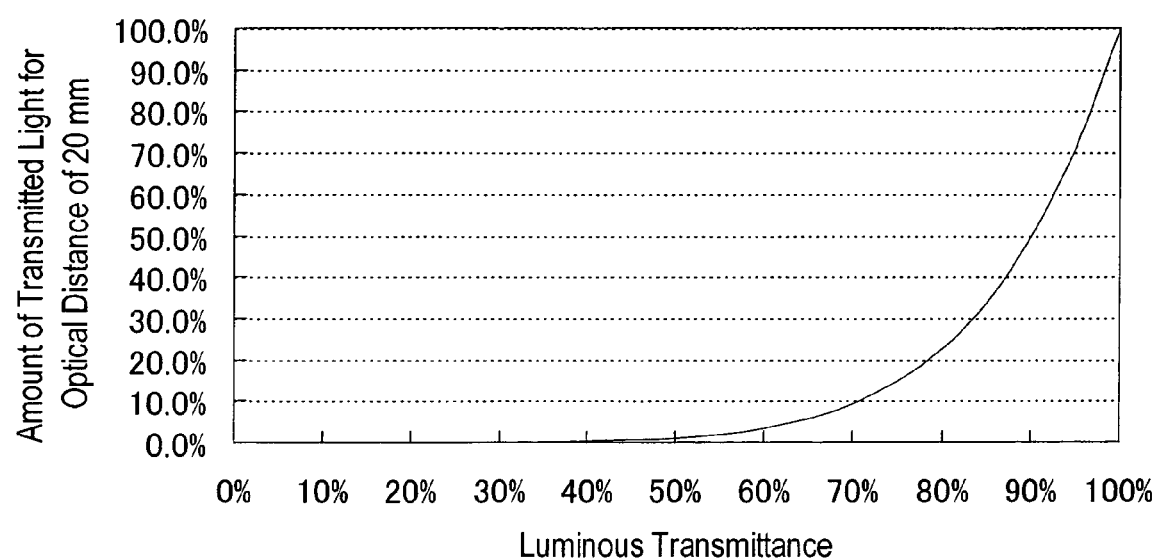
FIG. 3 is a graph showing the relationship between the luminous transmittance measured with a 3 mm thick test piece and the amount of transmitted light for an optical distance of 20 mm.

FIG. 3 shows the luminous transmittance (the transmittance with a 3 mm thick test piece) converted into the amount of transmitted light for an optical distance of about 20 mm, and Table 1 below shows representative values from the conversion. Note that in FIG. 3 and in Table 1, the amount of transmitted light is given as a percentage with respect to the amount of incident light.

TABLE 1

| | | | | |
|---|---|---|---|---|
| Luminous transmittance | 100.0% | 90.0% | 80.0% | 70.0% |
| Amount of transmitted light for optical distance of 20 mm | 100.0% | 49.5% | 22.6% | 9.3% |

As can be seen from FIG. 3, the value of the luminous transmittance more greatly contributes to the decrease in the amount of transmitted light as the optical distance is longer. As shown in FIG. 3 and Table 1, for luminous transmittance values of approximately 70%, 80% and 90%, the amounts of transmitted light are about 10% (9.3%), about 20% (22.6%) and about 50% (49.5%), respectively. Therefore, if the luminous transmittance of the resin used in the optical material is about 70% or more, an amount of transmitted light of about 10% or more can be realized, thereby obtaining a preferable optical characteristic as a diffusion plate. Moreover, if the luminous transmittance of the resin is about 80% or more, an amount of transmitted light of about 20% or more can be realized, thereby obtaining a more preferable optical characteristic. Furthermore, if the luminous transmittance of the resin is about 90% or more, an amount of transmitted light of about 50% or more can be realized, thereby obtaining an even more preferable optical characteristic.

Specifically, the resin used in the optical material may be an acrylic resin, polycarbonate, polyvinyl chloride, polystyrene, an MS resin (methyl methacrylate-styrene copolymer resin), or the like. Table 2 below shows the luminous transmittance values of these resins. Note that Table 2 shows approximate value ranges since the luminous transmittance of a resin slightly varies depending on the molding method, etc.

TABLE 2

|  | Luminous transmittance (%) |
| --- | --- |
| Acrylic resin | 92 to 93 |
| Polycarbonate | 86 to 87 |
| Polyvinyl chloride | 72 to 87 |
| Polystyrene | 87 to 92 |

As shown in Table 2, a luminous transmittance of about 70% or more can be obtained with polyvinyl chloride, and a luminous transmittance of about 80% or more can be obtained with polycarbonate. Moreover, a luminous transmittance of about 90% or more can be obtained with an acrylic resin, and a luminous transmittance of about 80% or more, or about 90% or more, can be obtained with polystyrene. Note that Table 2 does not show luminous transmittance values for an MS resin. An MS resin has physical properties, and achieves luminous transmittance values, generally in the middle between those of an acrylic resin and those of polystyrene.

Of course, the present invention is not limited to the resins mentioned herein, but may use any other suitable resin having a luminous transmittance of about 70% or more. However, since an acrylic resin, polycarbonate, polyvinyl chloride, polystyrene and an MS resin, which are mentioned herein, all have desirable moldability, it is preferred to use these resins in order to facilitate the molding of an optical element (herein, a diffusion plate). An acrylic resin is highly transparent (gives a high luminous transmittance) and inexpensive, and is thus preferable in terms of both the transmittance and the cost. Note however that since an acrylic resin absorbs water and expands, it may cause problems such as deformation of the component. In contrast, polycarbonate and polystyrene have lower transmittance values than an acrylic resin, but do not easily absorb water, whereby they are unlikely to cause problems such as deformation due to water absorption and can advantageously be used under high-humidity conditions. An MS resin has a well-balanced combination of these properties, i.e., has a high transmittance and does not easily absorb water. Therefore, with an MS resin, it is possible to prevent deformation due to water absorption while maintaining a high transmittance. Polycarbonate can advantageously be used under high-temperature conditions as the highest temperature it can withstand is about 30° C. higher than that an acrylic resin can withstand. For example, the deflection temperature under a load of about 4.6 kg/cm$^2$ is about 74° C. to about 113° C. for an acrylic resin and about 138° C. to about 142° C. for polycarbonate. Moreover, the deflection temperature under a load of about 18.6 kg/cm$^2$ is about 68° C. to about 102° C. for an acrylic resin and about 121° C. to about 132° C. for polycarbonate. Note that the deflection temperature under load is measured in accordance with ASTM D648.

Next, the reason why a desirable heat-radiating property is obtained with the thermal conductivity of a filler having a value of about 3 W/m·K or more will be explained, after explaining the reason why a desirable heat-radiating property cannot be obtained by mixing minute glass particles in a diffusion plate as disclosed in Japanese Laid-Open Patent Publication No. 4-172319.

In a typical diffusion plate, particles for exhibiting a light-diffusing property are mixed in a resin matrix in an amount of about 5% by mass. While the amount of particles to be mixed in of course varies to some extent depending on the degree of the light-diffusing property (defined by the haze value, for example), if it significantly exceeds about 5% by mass, the haze value will be excessively high, thereby increasing the distance over which light travels through the diffusion plate and significantly lowering the transmittance. Table 3 below shows the thermal conductivity of the minute glass particles, the thermal conductivity of the resin matrix, and the thermal conductivity of the diffusion plate as a whole when the minute glass particles are mixed in the resin matrix in an amount of about 5% by mass. Note that the thermal conductivity of a typical resin matrix is generally about 0.2 or less though it varies depending on the type of the resin.

TABLE 3

|  | Thermal conductivity (W/m · K) | Content (% by mass) |
| --- | --- | --- |
| Minute glass particles | 0.75 | 5 |
| Resin matrix | 0.20 | 95 |
| Diffusion plate as a whole | 0.23 | 100 |

As shown in Table 3, the thermal conductivity of the minute glass particles is on the same order of magnitude as that of the resin matrix. Even with such minute glass particles added in an amount of about 5% by mass, the thermal conductivity of the diffusion plate as a whole is substantially the same as that of the resin matrix. Thus, the heat-radiating property of a diffusion plate is not substantially improved by dispersing minute glass particles in a diffusion plate.

In a large-size liquid crystal display device (e.g., a liquid crystal display television having a diagonal size of about 32 inches, which is becoming the mainstream in the market), the power consumed by the backlight is as high as 100 W. Since most of the power consumed by the backlight is turned into heat and only little of it is converted into light for direct contribution to the display, it can be considered that substantially all of 100 W is turned into heat.

The display plane of a 32" liquid crystal display television has an area of about 0.72×0.41≈0.300 m$^2$, and the principal plane of a diffusion plate also has about the same area. Since the light source, being a heat source, radiates heat toward the diffusion plate and toward the opposite side, it can be considered that the diffusion plate will continue to receive a thermal energy of about 50 W onto a surface having an area of about 0.300 m². Thus, the temperature difference between the light source side of a 20 mm thick diffusion plate and the opposite side is expressed as follows.

Temperature difference (K)={Amount of heat supplied (50 W)×Thickness of diffusion plate (0.02 m)}/{Thermal conductivity (W/m·K)×Area of thermal conduction (0.3 m²)}

In view of the marketability, a liquid crystal display device should preferably have an internal temperature less than about 60° C. even under an approximately 50° C. environment. This is because the luminous efficiency of a cold cathode fluorescent tube (CCFT), commonly used as the light source, peaks at a temperature around 60° C., and the resin material starts softening when the temperature exceeds about 70° C. Therefore, the temperature difference needs to be less than about 10° C.

Where a filler is not mixed in a resin matrix, the temperature difference is as large as about 16° C. Even if minute glass particles are mixed in a resin matrix in an amount of about 5% by mass, the temperature difference is still about 14.5° C.

In contrast, if the thermal conductivity of the filler 3b is about 3 W/m·K or more, as in the diffusion plate 3 of the present preferred embodiment, the temperature difference can be made less than about 10° C. by mixing in the filler in an amount of about 5% by mass. If the thermal conductivity of the filler 3b is about 10 W/m·K or more, the temperature difference can be made less than about 5° C., thereby further increasing the margin.

Thus, if the diffusion plate 3 is made of an optical material including a resin having a luminous transmittance of about 70% or more and a filler mixed therein having a thermal conductivity of about 3 W/m·K or more, it is possible to obtain both a preferable optical characteristic as an optical element and a desirable heat-radiating property. Therefore, the illuminator 10A of the present preferred embodiment can realize a high luminous efficiency while minimizing softening of resin-made components. Moreover, with a liquid crystal display device including the illuminator 10A, it is possible to minimize the decrease in the display quality due to a temperature distribution non-uniformity of the liquid crystal display panel 20 and to produce a high-quality display.

Specifically, the filler 3b may be made of alumina (Al₂O₃), magnesium oxide (MgO), or other suitable material. Table 4 below shows the thermal conductivity of the filler 3b made of alumina, and thermal conductivity of the diffusion plate 3 as a whole in which the alumina filler 3b is mixed in the resin matrix 3a in an amount of about 5% by mass. Moreover, Table 5 below shows the thermal conductivity of the filler 3b made of magnesium oxide, and the thermal conductivity of the diffusion plate 3 as a whole in which the magnesium oxide filler 3b is mixed in the resin matrix 3a in an amount of about 5% by mass.

TABLE 4

|  | Thermal conductivity (W/m · K) | Content (% by mass) |
| --- | --- | --- |
| Alumina filler | 20.00 | 5 |
| Resin matrix | 0.20 | 95 |

TABLE 4-continued

|  | Thermal conductivity (W/m · K) | Content (% by mass) |
| --- | --- | --- |
| Diffusion plate as a whole | 1.19 | 100 |

TABLE 5

|  | Thermal conductivity (W/m · K) | Content (% by mass) |
| --- | --- | --- |
| Magnesium oxide filler | 60.00 | 5 |
| Resin matrix | 0.20 | 95 |
| Diffusion plate as a whole | 3.19 | 100 |

As shown in Table 4, the filler 3b made of alumina has a thermal conductivity of about 20 W/m·K, greater than that of the resin matrix 3a by a factor of about 100, whereby only with about 5% by mass of the filler 3b, the thermal conductivity of the diffusion plate 3 as a whole can be increased by a factor of about 6 from that of the resin matrix 3a.

As shown in Table 5, the filler 3b made of magnesium oxide has a thermal conductivity of about 60 W/m·K, greater than that of the resin matrix 3a by a factor of about 300, whereby only with approximately 5% by mass of the filler 3b, the thermal conductivity of the diffusion plate 3 as a whole can be increased by a factor of about 16 from that of the resin matrix 3a.

Alumina and magnesium oxide not only have a high thermal conductivity as described above, but also are inexpensive. Moreover, as can be seen from that fact that these materials are components of precious stones, they are highly transparent and can suitably be used as materials of the filler 3b. Alternatively, diamond may be used as a material of the filler 3b. Diamond has a very high thermal conductivity of about 2,000 W/m·K, and has a very high transparency. Of course, the present invention is not limited to these materials, but may use any other suitable material having a thermal conductivity of about 3 W/m·K or more. For example, yttrium oxide, gadolinium, lead tungstate, and other suitable materials, may be used. Note however that the filler 3b preferably also has a high transparency in order to maintain a high transparency of the diffusion plate 3 as a whole, and it is preferred that the filler 3b has a transparency as high as, or higher than, that of the resin matrix 3a. The filler 3b made of alumina, magnesium oxide or diamond has a higher transparency than that of the resin matrix 3a.

An optical material used for the diffusion plate 3 may be produced by a known method using a resin and a filler as described above. Specifically, the optical material can be obtained by preparing a resin and a filler as described above, and then dispersing the filler in the resin.

The filler can be produced by a known filler-making method using a filler material as described above. The particle diameter and the content of the filler can be appropriately determined based on an intended thermal conductivity (that of the diffusion plate 3 as a whole), an intended haze value, etc.

Since the wavelength of visible light is 350 nm to 800 nm, a filler whose particle diameter is on the same order of magnitude as visible light wavelengths (i.e., on the order of about 100 nm) can contribute to the diffusion of light. In other words, the particle diameter of a filler is preferably about 100 nm or more in order to realize a light-diffusing property. Moreover, in order to realize a preferable light-diffusing property, the diameter of each filler particle is preferably on an higher order of magnitude than the visible light wavelengths, and is preferably about 1 µm or more. Therefore, the average particle diameter of the filler is preferably about 1 µm or more, and more preferably about 2 µm.

In a conventional diffusion plate, a preferable light-diffusing property is realized by mixing silica beads in an acrylic resin matrix material in an amount of about 1% by mass to about 5% by mass. Assuming the particle diameter is constant, the light-diffusing property is generally proportional to the volume concentration of the particles. Therefore, where a filler having generally the same particle diameter as silica beads, it is possible to realize a preferable light-diffusing property by setting the volume concentration of the filler to be generally the same as that of silica beads in the conventional diffusion plate. Since the density of an acrylic resin is 1.1 g/cm$^3$ and the density of silica beads is 2.1 g/cm$^3$, the volume concentration of silica beads in the conventional diffusion plate is about 0.5% by volume to about 2.7% by volume. Therefore, it is possible to realize a preferable light-diffusing property by setting the volume concentration of the filler to be about 0.5% by volume or more and about 2.7% by volume or less. Where a filler made of alumina is used, for example, the filler is preferably mixed in the resin material in an amount of about 1% by mass to about 9% by mass since the density of alumina is 3.6 g/cm$^3$. Note that if the filler content is increased, the light-diffusing property increases but the light transmittance decreases. Moreover, when the filler content is increased, the moldability of the diffusion plate 3 may decrease in some cases. The filler content can be determined taking these factors into consideration.

The diffusion plate 3 can be formed by a known method such as injection molding using an optical material produced as described above. In order to sufficiently diffuse light output from the light sources 1 to minimize the brightness non-uniformity, the haze value of the diffusion plate 3 is preferably about 95% or more, more preferably, about 99% or more, and most preferably substantially 100%. Note that the haze value is measured by using, for example, aforementioned HR-100 manufactured by Murakami Color Research Laboratory.

Preferred Embodiment 2

Figure 4:
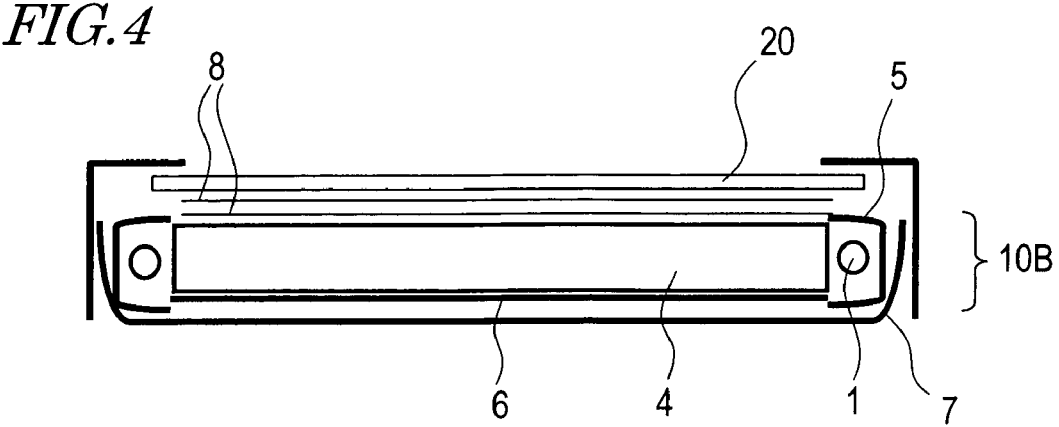
FIG. 4 is a cross-sectional view schematically illustrating another illuminator 10B according to a preferred embodiment of the present invention.

Referring to FIG. 4, an illuminator 10B of the present preferred embodiment will now be described. The illuminator 10B is also a backlight provided on the back side (the side away from the viewer) of the liquid crystal display panel 20.

The illuminator 10B is an edge light-type backlight, and includes the rod-shaped light sources 1, and a lightguide plate (lightguide) 4 for guiding light from the rod-shaped light sources 1 to the liquid crystal display panel 20, as illustrated in FIG. 4. In the present preferred embodiment, the rod-shaped light sources 1 are cold cathode fluorescent tubes (CCFTs). A reflector 5 and a reflection sheet 6 are provided near the rod-shaped light sources 1 and on the back side of the lightguide plate 4 (the opposite side of the lightguide plate 4 with respect to the liquid crystal display panel 20), respectively. The rod-shaped light sources 1, the lightguide plate 4, the reflector 5 and the reflection sheet 6 are accommodated in a chassis 7. Moreover, optical sheets 8 for adjusting the characteristics of light output from the lightguide plate 4 are provided between the lightguide plate 4 and the liquid crystal display panel 20.

Figure 5:
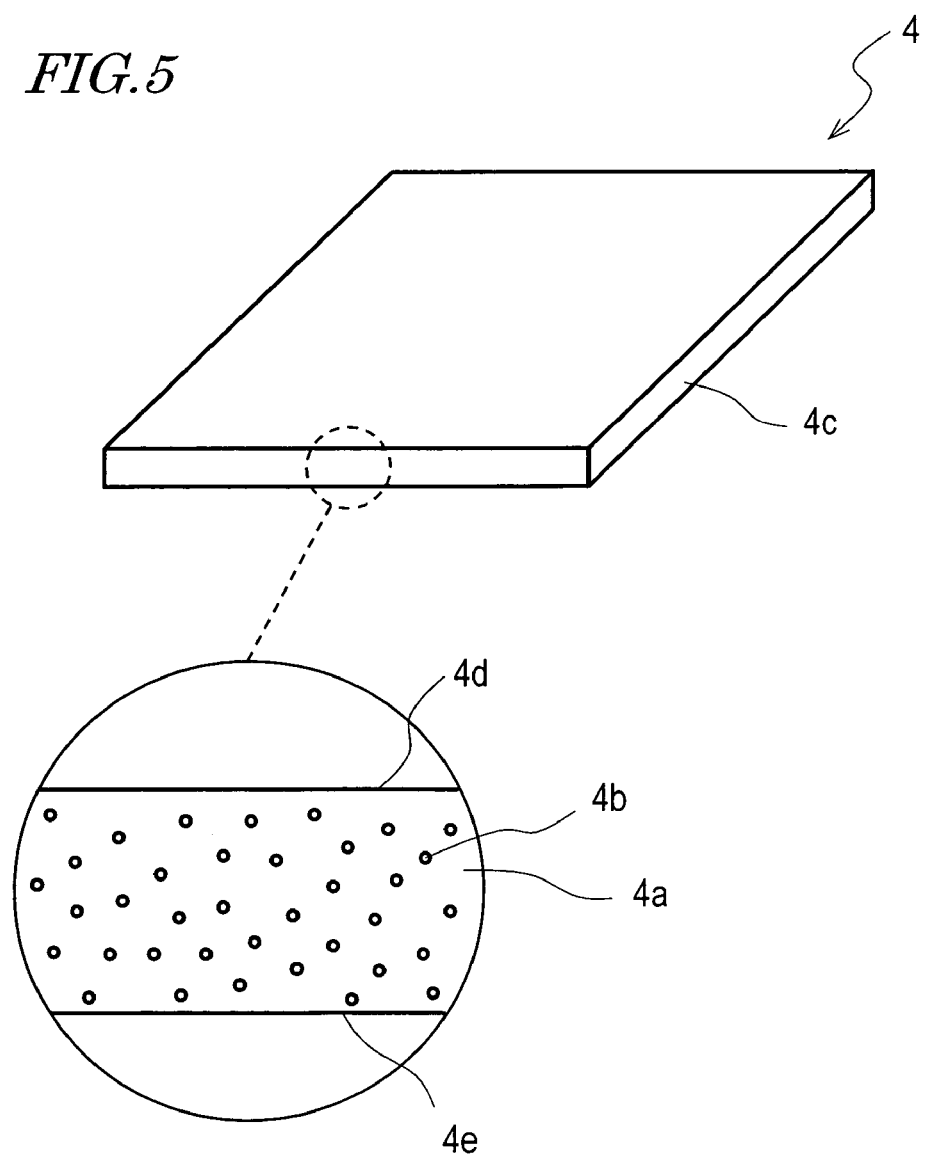
FIG. 5 schematically illustrates a lightguide plate 4 provided in the illuminator 10B according to a preferred embodiment of the present invention.

The illuminator 10B of the present preferred embodiment is the same in structure as a known edge light-type backlight except that the lightguide plate 4 is made of an optical material different from those used conventionally. Referring to FIG. 5, the lightguide plate 4 of the illuminator 10B will now be described.

The lightguide plate 4 includes a resin matrix 4a and a filler 4b dispersed in the resin matrix 4a, as illustrated in FIG. 5. The filler 4b used in the present preferred embodiment is preferably particulate but may be other suitable materials.

Moreover, the lightguide plate 4 has an input-side surface 4c for receiving light output from the rod-shaped light sources 1, an exit-side surface 4d through which light coming from the input-side surface 4c and traveling through the lightguide plate 4 is output toward the liquid crystal display panel 20, and an opposing surface 4e opposing the exit-side surface 4d. Although not shown in FIG. 5, at least one of the exit-side surface 4d and the opposing surface 4e is provided with a light-distribution-controlling structure for taking out light traveling through the lightguide plate 4 toward the liquid crystal display panel 20. The light-distribution-controlling structure may be one of those used in known lightguide plates. Specifically, the light-distribution-controlling structure may be a prism, a lens, creases, or the like.

The lightguide plate 4 is preferably made of an optical material including a resin having a luminous transmittance of about 70% or more and a filler mixed therein having a thermal conductivity of about 3 W/m·K or more. Therefore, for the same reasons described above in the explanation of Preferred Embodiment 1 for the diffusion plate 3, the lightguide plate 4 has a preferable optical characteristic as an optical element and a desirable heat-radiating property. Therefore, the illuminator 10B of the present preferred embodiment can realize a high luminous efficiency while minimizing softening of resin-made components. Moreover, with a liquid crystal display device including the illuminator 10B, it is possible to minimize the decrease in the display quality due to a temperature distribution non-uniformity of the liquid crystal display panel 20 and to produce a high-quality display.

An optical material for the lightguide plate 4 can be produced in a similar manner to that for the optical material for the diffusion plate 3 in Preferred Embodiment 1, and the lightguide plate 4 can be produced by a known lightguide plate production method using such an optical material.

Note that unlike the diffusion plate 3, the lightguide plate 4 does not need to have a light-diffusing property. Since the wavelength of visible light is 350 nm to 800 nm, the filler 4b having a particle diameter on a smaller order of magnitude than the wavelength range, i.e., a particle diameter less than about 100 nm, does not contribute to the light-diffusing property. Therefore, if the particle diameter of the filler 4b is set to be less than about 100 nm, it is possible to obtain the lightguide plate 4 that does not substantially have a light-diffusing property. Of course, the lightguide plate 4 may include the filler 4b having a particle diameter of about 1 µm or more and have a light-diffusing property. Also with optical elements other than the lightguide plate 4, it is possible to obtain an optical element having an intended light-diffusing property and an intended thermal conductivity by appropriately controlling the particle diameter of the filler 4b as described above. For example, by adding the filler 4b that does not contribute to the light-diffusing property to an optical material of the diffusion plate 3, it is possible to obtain the diffusion plate 3 with a low light-diffusing property (small haze value) and a high thermal conductivity.

Preferred Embodiment 3

Before describing the illuminator of the present preferred embodiment, the brightness non-uniformity problem with direct-type backlights will be discussed below.

Figure 21:
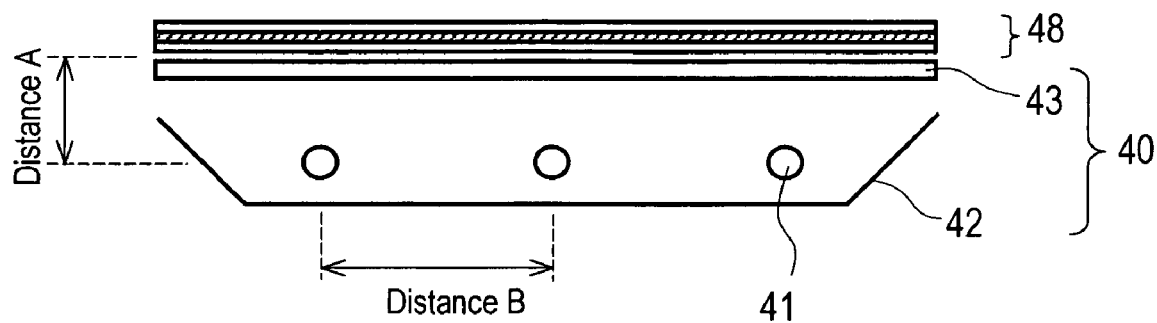
FIG. 21 is a cross-sectional view schematically illustrating a conventional direct-type backlight 40.

With the direct-type backlight 40 illustrated in FIG. 21, the light sources (fluorescent tubes) 41 are arranged so that the area extending in the direction perpendicular to the longitudinal direction of the light sources 41 is covered by the light sources 41 only in an interrupted (discrete) manner, thereby resulting in a brightness non-uniformity with the brightness being higher in areas directly above the light sources 41 and lower in other areas between the light sources 41.

The brightness non-uniformity is smaller as the distance A between the light sources 41 and the liquid crystal display panel 48 is larger and as the distance B between the light sources 41 is smaller. Therefore, the smaller the ratio R (=B/A) of the distance B with respect to the distance A is, the smaller the brightness non-uniformity is, and vice versa. Thus, it is possible to reduce the brightness non-uniformity by increasing the distance A between the light sources 41 and the liquid crystal display panel 48 or by increasing the number of the light sources 41 to shorten the distance B between the light sources 41.

However, an increase in the distance A between the light sources 41 and the liquid crystal display panel 48 leads to an increase in the thickness of the backlight 40, and thus the display device, thereby detracting from its commercial value. Moreover, an increase in the number of the light sources 41 to reduce the distance B between the light sources 41 leads to an increase in the cost, thereby also detracting from its commercial value.

Figure 6:
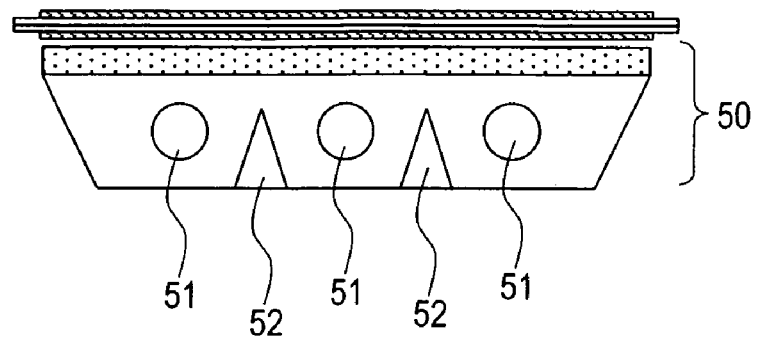
FIG. 6 is a cross-sectional view schematically illustrating a conventional direct-type backlight.

In view of this, Japanese Laid-Open Patent Publication No. 2002-122863 discloses a backlight 50 in which the light-reflecting protruding portions 52 having a triangular cross section are provided between light sources 51, as illustrated in FIG. 6, thereby minimizing the brightness non-uniformity.

Figure 7:
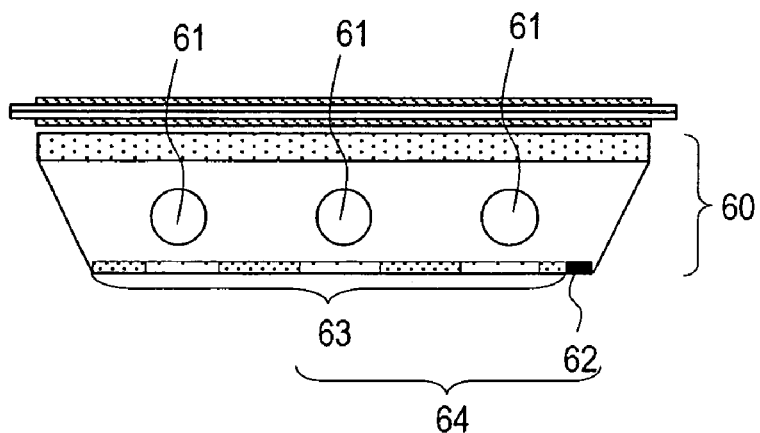
FIG. 7 is a cross-sectional view schematically illustrating a conventional direct-type backlight.

Moreover, Japanese Laid-Open Patent Publication No. 2000-310776 discloses a backlight 60 in which an auxiliary light source 64 including a primary light source 62 and a lightguide plate 63 is provided on one side of light sources 61 that is away from the liquid crystal display panel, as illustrated in FIG. 7, thereby minimizing the brightness non-uniformity. Japanese Laid-Open Patent Publication No. 2000-310776 also discloses an arrangement in which the light-scattering dot patterns on the surface of the lightguide plate 63 for taking out light that has entered the lightguide plate 63 from the primary light source 62 are arranged sparsely in areas directly under the light sources 61 and densely in other areas between the light sources 61, whereby the brightness of light from the lightguide plate 63 can be made lower in areas directly under the light sources 61 and higher in other areas between the light sources 61, thus further minimizing the brightness non-uniformity.

In-depth research conducted by the present inventor from various viewpoints on the relationship between the structure of a backlight and the degree of brightness non-uniformity revealed that the brightness non-uniformity is not sufficiently suppressed with the backlights disclosed in these publications. Specifically, with any of the backlights disclosed in these publications, although the brightness non-uniformity is sufficiently small in the normal direction (the direction normal to the display plane of the display device), it is not sufficiently small in an inclined direction (a direction inclined with respect to the display plane normal direction).

Figure 8:
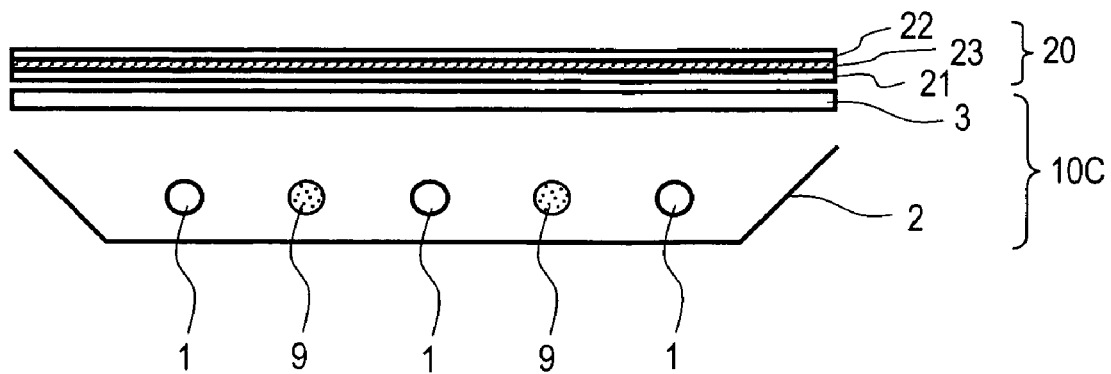
FIG. 8 is a cross-sectional view schematically illustrating a liquid crystal display device including another illuminator 10C according to a preferred embodiment of the present invention.

Now, an illuminator 10C of the present preferred embodiment will be described with reference to FIG. 8 and FIG. 9. FIG. 8 is a cross-sectional view schematically illustrating a liquid crystal display device including the illuminator 10C, and FIG. 9 is a plan view schematically illustrating the illuminator 10C.

Figure 9:
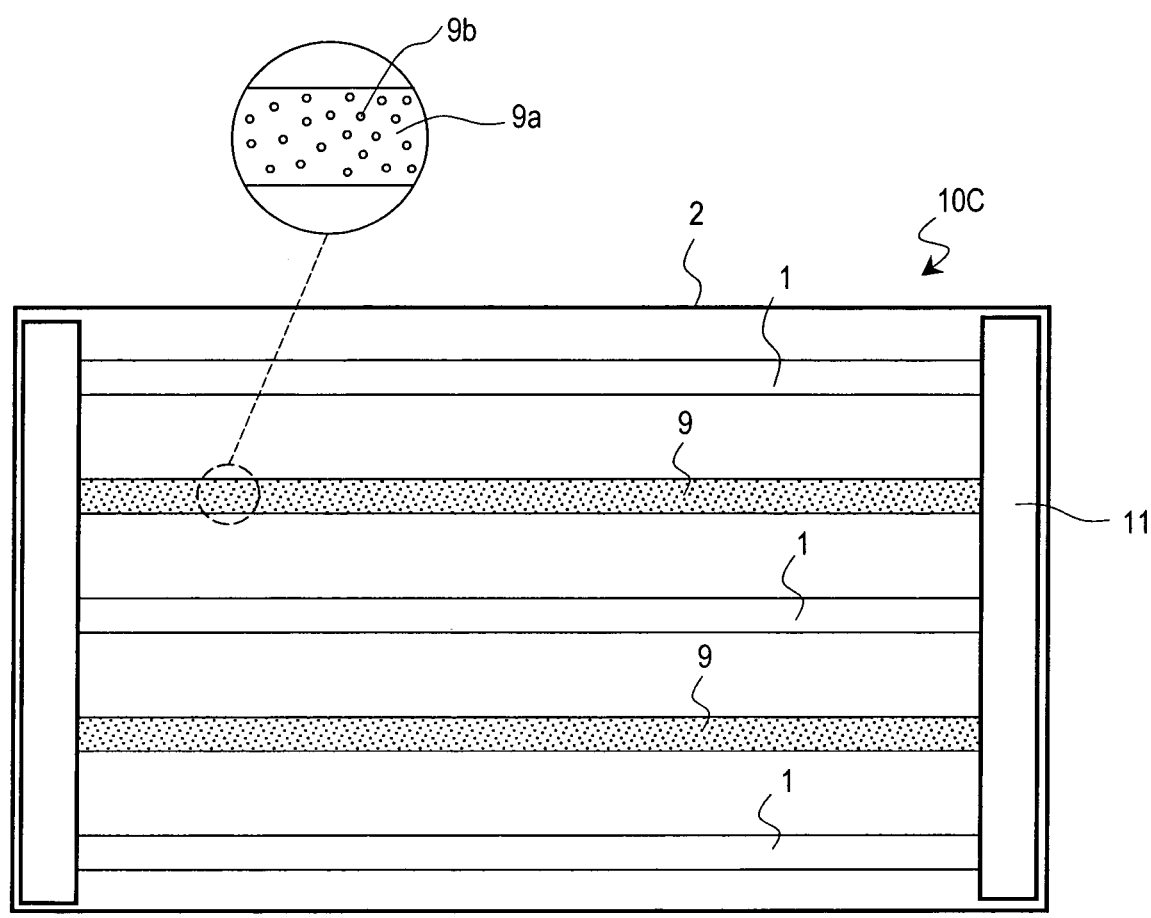
FIG. 9 is a plan view schematically illustrating the illuminator 10C according to a preferred embodiment of the present invention.

The illuminator 10C is a direct-type backlight provided on the back side (the side away from the viewer) of the liquid crystal display panel 20, as illustrated in FIG. 8, and includes a plurality of rod-shaped light sources 1 arranged generally parallel to one another, as illustrated in FIG. 8 and FIG. 9. In the present preferred embodiment, the rod-shaped light sources 1 are preferably cold cathode fluorescent tubes (CCFTs).

The rod-shaped light sources 1 are held in the case 2 by supporting members (holders) 11 provided in the case 2, as illustrated in FIG. 9, and an optical sheet 3 is provided between the rod-shaped light sources 1 and the liquid crystal display panel 20, as illustrated in FIG. 8. The optical sheet 3 may be, for example, a diffusion sheet or a prism sheet. Note that while only one optical sheet 3 is shown in FIG. 8, a diffusion sheet, a prism sheet, etc., are used in combination in practice. Typically, in order to increase the light efficiency, the surface of the case 2 that is closer to the rod-shaped light sources 1 is provided with a highly-reflective member (e.g., a light-reflecting sheet), or the case 2 itself is made of a highly-reflective material.

The illuminator 10C further includes a light-scattering member 9 for scattering light provided between two adjacent rod-shaped light sources 1. As illustrated in FIG. 9, the light-scattering member 9 includes a resin matrix $9a$ and a filler (inorganic filler) $9b$ dispersed in the resin matrix $9a$. The filler $9b$ used in the present preferred embodiment is particulate. The refractive index of the filler $9b$ is different from that of the resin matrix $9a$, whereby the light-scattering member 9 exhibits a light-scattering property (light-diffusing property). The light-scattering member 9 is preferably made of an optical material including a resin having a luminous transmittance of about 70% or more and a filler mixed therein having a thermal conductivity of about 3 W/m·K or more.

Each of the light-scattering members 9 of the present preferred embodiment is a rod-shaped member, and arranged generally in between two adjacent rod-shaped light sources 1 and generally parallel to the rod-shaped light sources 1. Moreover, the light-scattering members 9 are held in the case 2 by the supporting members 11, as are the rod-shaped light sources 1.

In the illuminator 10C of the present preferred embodiment, each light-scattering member 9 is disposed between two adjacent rod-shaped light sources 1, whereby portions of light output from the rod-shaped light sources 1 are scattered by the light-scattering member 9, thus increasing the intensity of light coming out from an area of the illuminator 10C between the rod-shaped light sources 1. Thus, it is possible to reduce the brightness non-uniformity. Since the light-scattering members 9 provided between the rod-shaped light sources 1 scatter light substantially in every azimuth direction, they not only function to increase the intensity of light coming out from areas between the rod-shaped light sources 1 but also function as pseudo light sources. Therefore, it is possible to realize an optical system similar to those realized with a larger number of rod-shaped light sources 1 arranged at shorter intervals. Thus, the brightness non-uniformity can be reduced not only in the normal direction (the direction normal to the display plane of the display device) but also in an inclined direction (a direction inclined with respect to the display plane normal direction).

The light-scattering member 9 is preferably made of an optical material including a resin having a luminous transmittance of about 70% or more and a filler mixed therein having a thermal conductivity of about 3 W/m·K or more. Therefore, for the same reasons described above in the description of Preferred Embodiment 1 for the diffusion plate 3, the light-scattering member 9 has preferable optical characteristics as an optical element and a desirable heat-radiating property. Therefore, the illuminator 10C of the present preferred embodiment can realize a high luminous efficiency while minimizing softening of resin-made components. Moreover, with a liquid crystal display device including the illuminator 10C, it is possible to minimize the decrease in the display quality due to a temperature distribution non-uniformity of the liquid crystal display panel 20 and to produce a high-quality display.

FIG. 10 to FIG. 13 illustrate how a brightness non-uniformity occurs in a conventional direct-type backlight, and how a brightness non-uniformity is minimized in the illuminator 10C of the present preferred embodiment.

Figure 10:
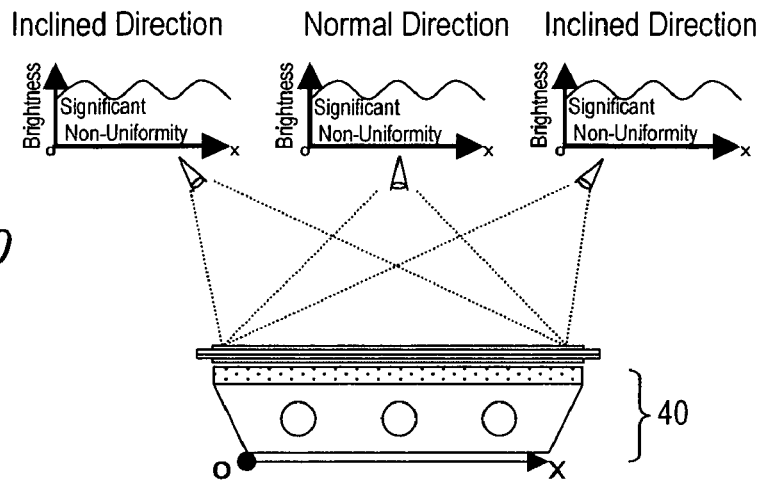
FIG. 10 schematically illustrates how a brightness non-uniformity occurs in a conventional direct-type backlight.

The typical conventional direct-type backlight 40 has a significant brightness non-uniformity both in the normal direction and in inclined directions, as illustrated in FIG. 10. Thus, the display quality is lowered.

Figure 11:
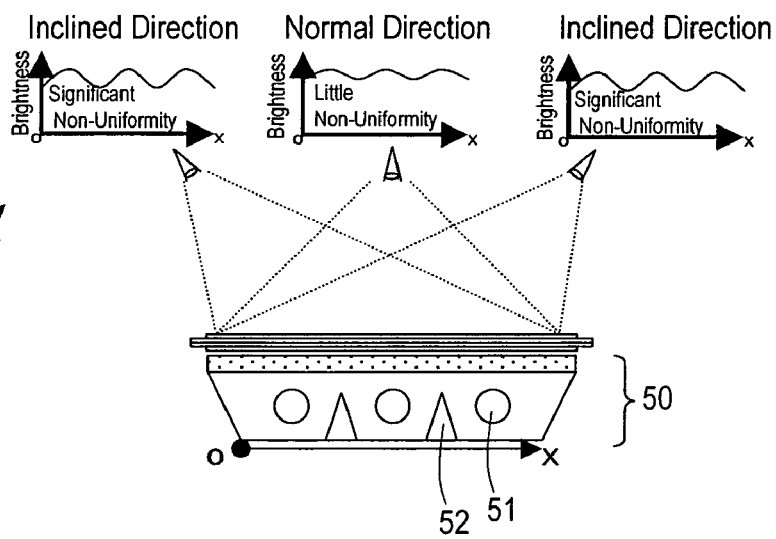
FIG. 11 schematically illustrates how a brightness non-uniformity occurs in a conventional direct-type backlight.

The backlight 50 disclosed in Japanese Laid-Open Patent Publication No. 2002-122863 includes the light-reflecting protruding portions 52 between the light sources 51, as illustrated in FIG. 11, thereby increasing the intensity of light coming out from areas between the light sources 51 and thus reducing the brightness non-uniformity in the normal direction. However, unlike the light-scattering members 9 capable of scattering light in every azimuth direction, the protruding portions 52, which have a triangular cross section and are light-reflecting, do not function as pseudo light sources, whereby it is not possible to sufficiently reduce the brightness non-uniformity in inclined directions. Thus, the display quality is not improved sufficiently.

Figure 12:
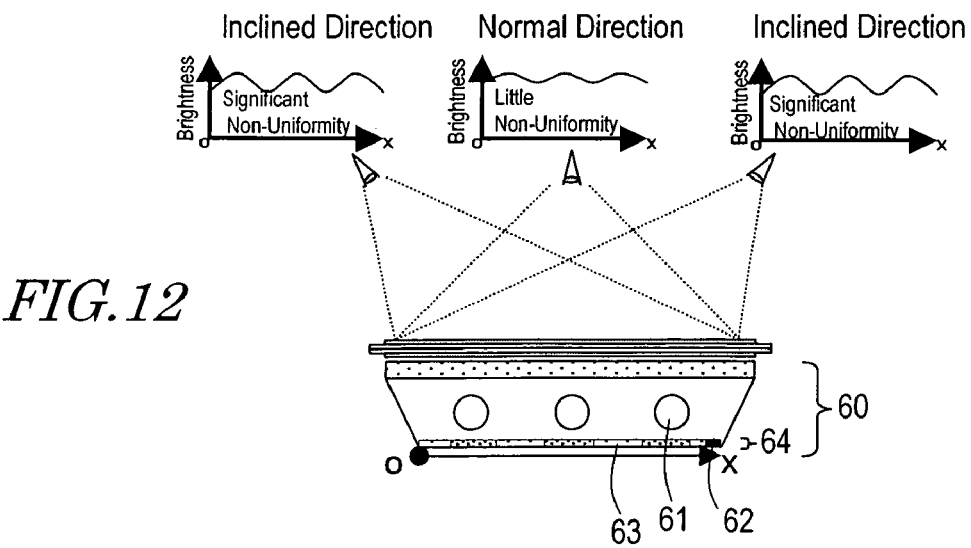
FIG. 12 schematically illustrates how a brightness non-uniformity occurs in a conventional direct-type backlight.

In the backlight 60 disclosed in Japanese Laid-Open Patent Publication No. 2000-310776, the auxiliary light source 64 is provided under the light source 61, as illustrated in FIG. 12, and the light-scattering dot patterns on the lightguide plate 63 of the auxiliary light source 64 are arranged sparsely in areas directly under the light sources 61 and densely in other areas between the light sources 61, thereby increasing the intensity of light coming out from areas between the light sources 61 and thus reducing the brightness non-uniformity in the normal direction. However, the auxiliary light source 64, which is disposed under, but not between, the light sources 61 and which gives a planar light emission, cannot function as a pseudo light source in cooperation with the rod-shaped light sources 61. Therefore, it is not possible to sufficiently reduce the brightness non-uniformity in inclined directions. Thus, the display quality is not improved sufficiently.

Figure 13:
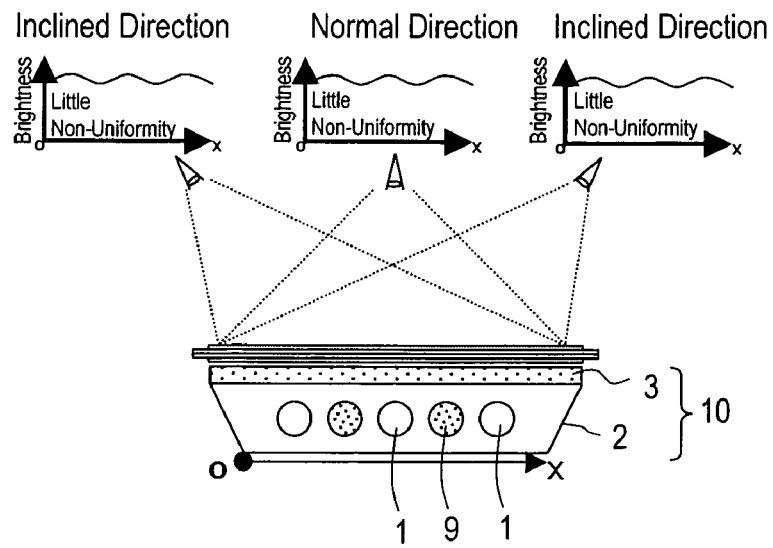
FIG. 13 schematically illustrates how a brightness non-uniformity is minimized in the illuminator 10C according to a preferred embodiment of the present invention.

In contrast, in the illuminator 10C of the present preferred embodiment, the light-scattering members 9 are disposed each between two adjacent rod-shaped light sources 1, as illustrated in FIG. 13, and thus the light-scattering members 9 can function as pseudo light sources, whereby it is possible to reduce the brightness non-uniformity not only in the normal direction but also in inclined directions. Thus, a display device including the illuminator 10C can produce a high-quality display. Moreover, since the light-scattering members 9 function as pseudo light sources, it is possible to reduce the distance between the liquid crystal display panel 20 and the rod-shaped light sources 1 (corresponding to the distance A in FIG. 21) without increasing the number of rod-shaped light sources 1. Therefore, the illuminator 10C has a high commercial value as it can be made in a thinner profile, and it can also be manufactured at a low cost.

Figure 14A:
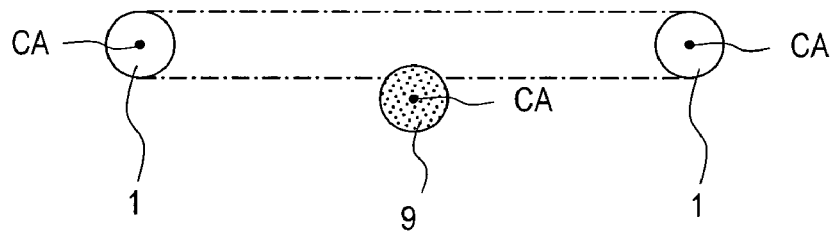
FIG. 14A, FIG. 14B and FIG. 14C each illustrate an arrangement of light-scattering members used in the illuminator 10C.
Figure 14B:
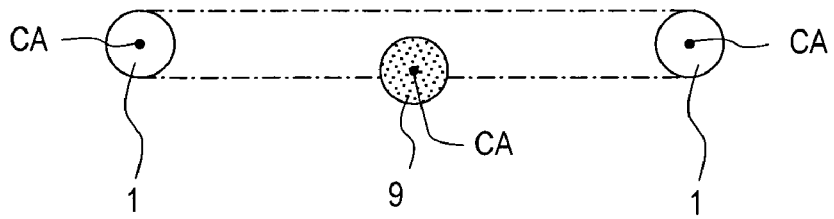
Figure 14C:
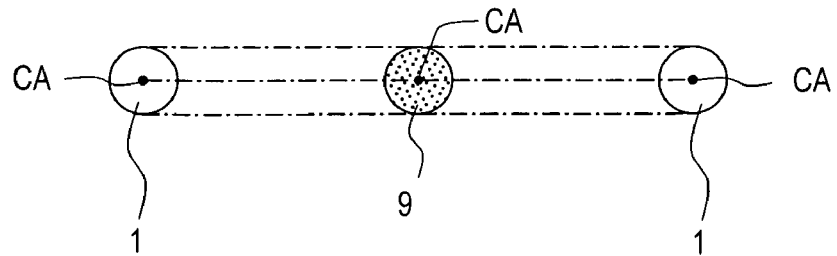

As described above, in the illuminator 10C, the light-scattering members 9 for scattering light can function as pseudo light sources because they are arranged while considering not only their planar positioning with the rod-shaped light sources 1 but also their three-dimensional positioning with the rod-shaped light sources 1. The light-scattering members 9 are located "between" the rod-shaped light sources 1 not only as viewed in the display plane normal direction, as illustrated in FIG. 9, but are also located "between" the rod-shaped light sources 1 as viewed in the longitudinal direction of the rod-shaped light sources 1, as illustrated in FIG. 8. Note that "the light-scattering members 9 being positioned between the rod-shaped light sources 1 as viewed in the longitudinal direction of the rod-shaped light sources 1" as used herein means that the light-scattering members 9 are at least partly included in the space defined between two rod-shaped light sources 1, as illustrated in FIG. 14A to FIG. 14C. In order to further reduce the brightness non-uniformity as viewed in inclined directions, it is preferred that the central axis (virtual axis) CA of each of the light-scattering members 9 is included in the space defined between the rod-shaped light sources 1, as illustrated in FIG. 14B, and it is more preferred that the central axis CA of each of the light-scattering members 9 is substantially coplanar with (at the same height as) the central axes CA of the rod-shaped light sources 1, as illustrated in FIG. 14C.

Moreover, in order for the light-scattering members 9 to function preferably as pseudo light sources, it is preferred that the light-scattering members 9 have light distribution characteristics close to those of the rod-shaped light sources 1. In order for the light-scattering members 9 to have light distribution characteristics close to those of the rod-shaped light sources 1, it is preferred that the light-scattering members 9 are rod-shaped members and that the rod-shaped light-scattering members 9 are arranged generally parallel to the rod-shaped light sources 1, as in the present preferred embodiment. Moreover, it is preferred that the rod-shaped light-scattering members 9 each have substantially the same outer diameter as that of the rod-shaped light source 1.

Figure 15A:
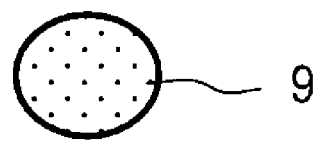
FIG. 15A to FIG. 15E each illustrate the shape of the cross section of the light-scattering member used in the illuminator 10C taken in a direction perpendicular to the longitudinal direction.
Figure 15B:
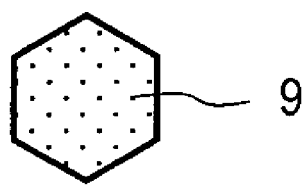
Figure 15C:
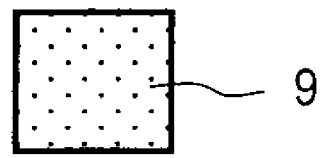
Figure 15D:
Figure 15E:
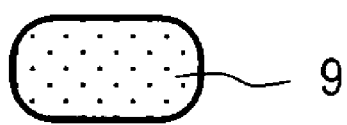

While the present preferred embodiment preferably includes the cylindrical light-scattering members 9 having a generally circular cross section in a direction perpendicular to the longitudinal direction, the shape of the cross section of the light-scattering members 9 is not limited to this. Alternatively, the shape of the cross section of the light-scattering members 9 perpendicular to the longitudinal direction may be a generally circular shape as illustrated in FIG. 15A, a generally regular polygonal shape as illustrated in FIG. 15B, or a generally rectangular shape as illustrated in FIG. 15C. It may also be a generally elliptical shape as illustrated in FIG. 15D, or a generally rectangular shape with circular arc corners as illustrated in FIG. 15E. Note however that in order to realize light distribution characteristics close to those of the rod-shaped light sources 1, it is preferred that the shape of the cross section of the light-scattering members 9 taken in a direction perpendicular to the longitudinal direction is generally the same as that of the rod-shaped light sources 1. Since a typical rod-shaped light source such as a cold cathode fluorescent tube often has a generally circular cross section, it is preferred from that point of view that the shape of the cross section of the light-scattering members 9 taken in a direction perpendicular to the longitudinal direction is generally circular.

Note that while only one of each of the light-scattering members 9 is provided between two adjacent rod-shaped light sources 1 in the present preferred embodiment, more than one of the light-scattering members 9 may be provided between two adjacent rod-shaped light sources 1. Where one light-scattering member 9 is provided between two adjacent rod-shaped light sources 1, as in the present preferred embodiment, it is preferred that the light-scattering member 9 is located generally in the middle between the two rod-shaped light sources 1. If the light-scattering member 9 is located generally in the middle between two adjacent rod-shaped light sources 1, it is possible to increase the effect of minimizing the brightness non-uniformity.

The degree to which the light-scattering members 9 scatter light is defined by the haze value, for example. The specific haze value of the light-scattering members 9 may be appropriately determined based on the number of rod-shaped light sources 1, the distance between the rod-shaped light sources 1, the brightness of each rod-shaped light source 1, etc.

Figure 16:
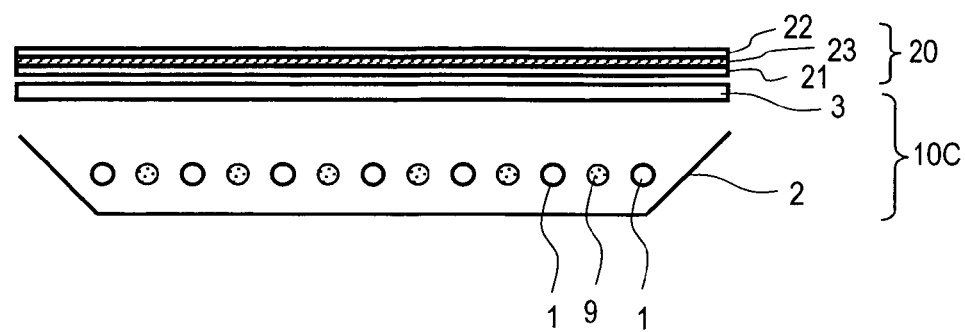
FIG. 16 is a cross-sectional view schematically illustrating a variation of the illuminator 10C.
Figure 17:
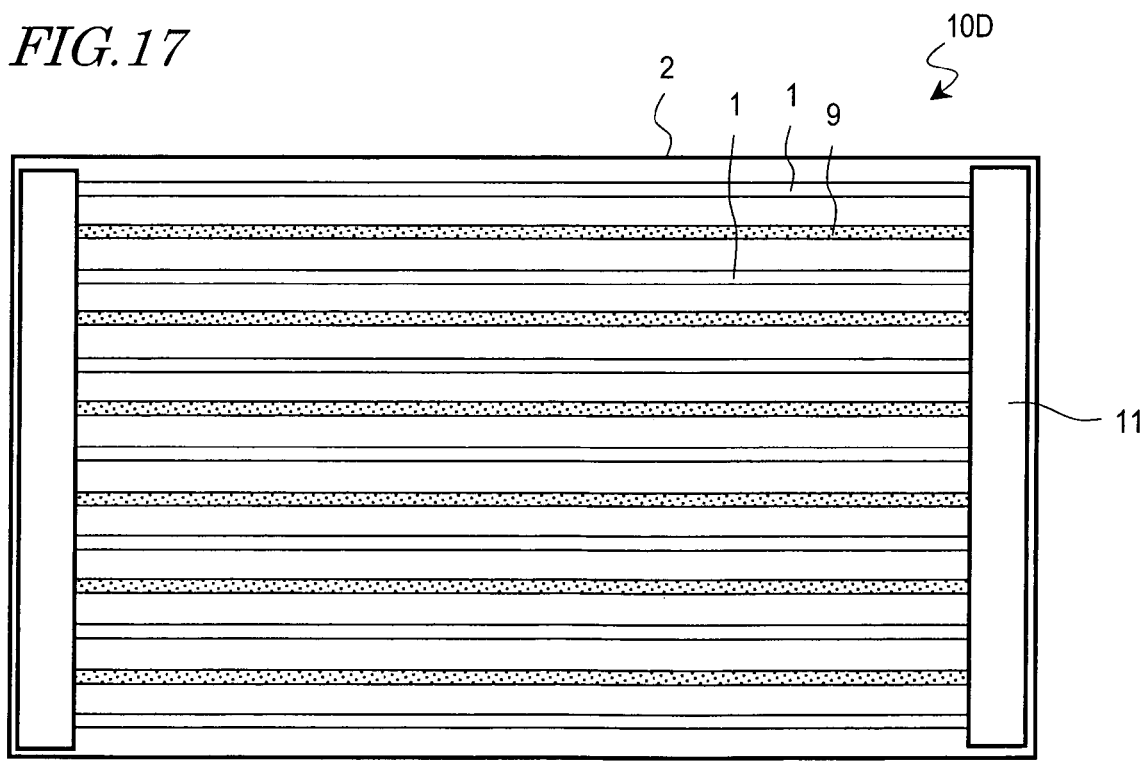
FIG. 17 is a plan view schematically illustrating the variation of the illuminator 10C.

Note that three rod-shaped light sources 1 are provided in the example illustrated in FIG. 8 and FIG. 9, it is understood that the number of the rod-shaped light sources 1 is not limited to this. A larger number of rod-shaped light sources 1 may be provided, as illustrated in FIG. 16 and FIG. 17.

Figure 18:
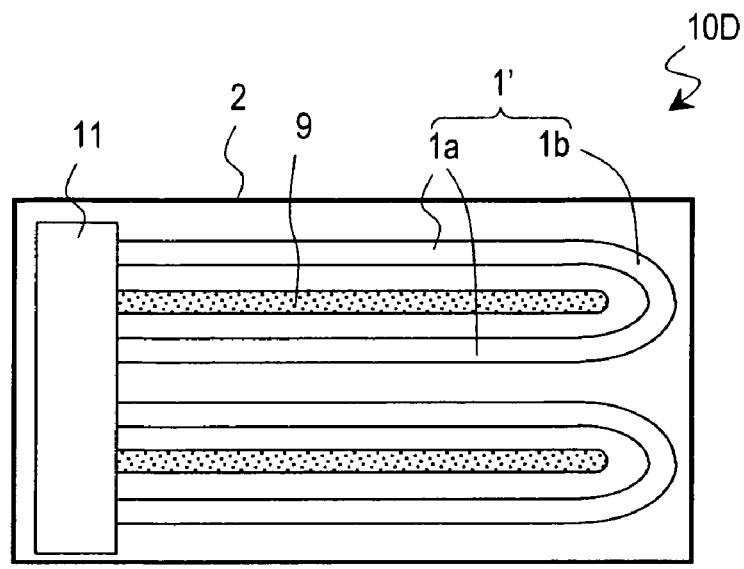
FIG. 18 is a plan view schematically illustrating the illuminator 10D according to a preferred embodiment of the present invention.

Referring to FIG. 18, another illuminator 10D of the present preferred embodiment will be described. The illuminator 10D includes U-shaped light sources 1', as illustrated in FIG. 18. Each light source 1' includes a plurality of rod-shaped portions (rod-shaped light emitting portions) 1a arranged generally parallel to each other, and a bent portion 1b connecting the two adjacent rod-shaped portions 1a to each other. The light sources 1' of the present preferred embodiment are cold cathode fluorescent tubes.

The illuminator 10D further includes the light-scattering members 9 for scattering light each between two adjacent rod-shaped portions 1a. The light-scattering members 9 of the present preferred embodiment are rod-shaped members, and arranged generally in the middle between two adjacent rod-shaped portions 1a and generally parallel to the rod-shaped portions 1a.

The light sources 1' and the light-scattering members 9 are held in the case 2 by the supporting member (holder) 11 provided in the case 2. Although not shown in the figure, an optical sheet is provided as necessary in a more frontward position (closer to the viewer) than the light sources 1' and the light-scattering members 9.

Also in the illuminator 10D, the light-scattering members 9 each disposed between two adjacent rod-shaped portions 1a function as pseudo light sources, whereby it is possible to realize an optical system similar to those realized with a larger number of rod-shaped portions 1a of the light sources 1 arranged at shorter intervals. Thus, the brightness non-uniformity can be reduced not only in the normal direction but also in an inclined direction.

As to the preferred shapes and arrangements of the light-scattering members 9 of the illuminator 10D, the description for the light-scattering members 9 of the illuminator 10C applies substantially as it is. Specifically, in order to further reduce the brightness non-uniformity as viewed in inclined directions, it is preferred that the central axis (virtual axis) of each of the light-scattering members 9 is included in the space defined between two rod-shaped portions 1a, and it is more preferred that the central axis of each of the light-scattering members 9 is substantially coplanar with (at the same height as) the central axes of the rod-shaped portions 1a.

Moreover, in order for the light-scattering members 9 to function preferably as pseudo light sources, it is preferred that the light-scattering members 9 have light distribution characteristics close to those of the rod-shaped portions 1a. In order for the light-scattering members 9 to have light distribution characteristics close to those of the rod-shaped portions 1a, it is preferred that the light-scattering members 9 are rod-shaped members and that the rod-shaped light-scattering members 9 are arranged generally parallel to the rod-shaped portions 1a, as in the present preferred embodiment. Moreover, it is preferred that the rod-shaped light-scattering members 9 each have substantially the same outer diameter as that of the rod-shaped portion 1a. Furthermore, it is preferred that the shape of the cross section of the light-scattering member 9 taken in a direction perpendicular to the longitudinal direction is substantially the same as that of the rod-shaped portion 1a, and it is preferred that the shape of the cross section of the light-scattering member 9 is generally circular since the rod-shaped portion of a commonly-used light source such as a cold cathode fluorescent tube typically has a generally circular cross-sectional shape.

Moreover, where one light-scattering member 9 is provided between two rod-shaped portions 1a, as in the present preferred embodiment, it is preferred that the light-scattering member 9 is located generally in the middle between two rod-shaped portions 1a.

While the present preferred embodiment is directed to the U-shaped light source 1' including two rod-shaped portions 1a and one bent portion 1b, a light source including more rod-shaped portions and more bent portions may be used instead of the U-shaped light source 1'. For example, a W-shaped light source including four rod-shaped portions and three bent portions may be used. With a light source including a plurality of rod-shaped portions and bent portions each connecting two rod-shaped portions to each other, it is possible to reduce the number of light sources as compared with a case where rod-shaped light sources are used, thereby reducing the cost.

While a diffusion plate for an illuminator, a lightguide plate (lightguide) and a light-scattering member for an illuminator have been illustrated in Preferred Embodiments 1 to 3 above as optical elements of the present invention, the present invention is not limited thereto and can be used with optical elements in general. If an optical element is made of an optical material including a resin having a luminous transmittance of about 70% or more and a filler mixed therein having a thermal conductivity of about 3 W/m·K or more, it is possible to obtain both a preferable optical characteristic (transparency) as an optical element and a desirable heat-radiating property.

Figure 19A:
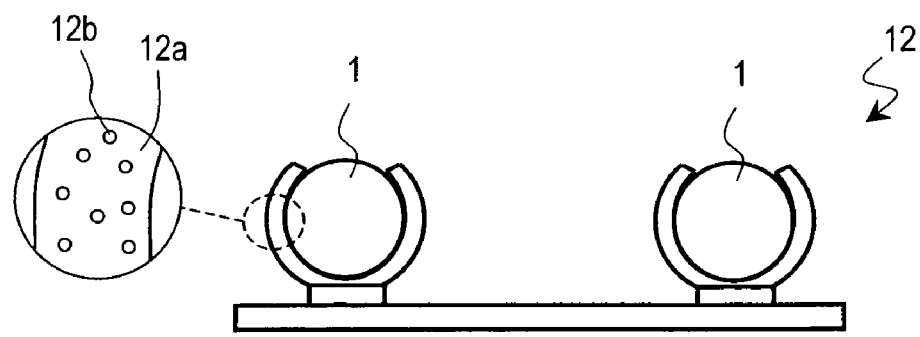
FIG. 19A and FIG. 19B are cross-sectional views each schematically illustrating a light source holder made of an optical material according to a preferred embodiment of the present invention.
Figure 19B:
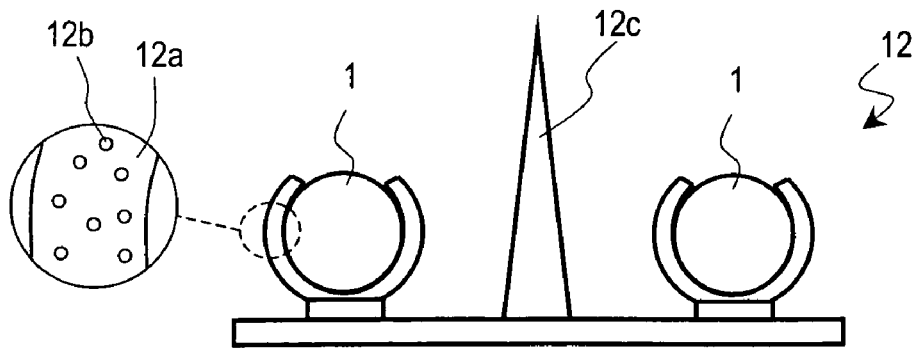

The optical material of various preferred embodiments of the present invention can also be used as a material of a light source holder (light source supporting member) for an illuminator (e.g., a direct-type backlight). FIG. 19A and FIG. 19B each illustrate a light source holder 12 made of an optical material including a resin having a luminous transmittance of about 70% or more and a filler mixed therein having a thermal conductivity of about 3 W/m·K or more. The holder 12 is a member for holding the rod-shaped light source 1, and includes a resin matrix 12a and a filler (inorganic filler) 12b dispersed in the resin matrix 12a. Note that the holder 12 illustrated in FIG. 19B differs from that illustrated in FIG. 19A in that the holder 12 illustrated in FIG. 19B includes a protruding portion 12c having a triangular cross section. The protruding portion 12c is provided for supporting optical elements, such as a diffusion plate, located above the light source.

Conventionally, light-blocking white resin materials have been used in light source holders. However, a holder made of such a material has a low thermal conductivity and allows the heat from a rod-shaped light source to stay therein, thereby lowering the reliability of the device and causing optical non-uniformities.

In contrast, with the holders 12 illustrated in FIG. 19A and FIG. 19B, heat from the rod-shaped light source 1 can be quickly radiated, whereby it is possible to improve the reliability of the device and reduce optical non-uniformities. Moreover, since the holder 12 is highly transparent, much of the light output from the rod-shaped light source 1 can be transmitted therethrough, whereby it is possible to improve the brightness.

Figure 20A:
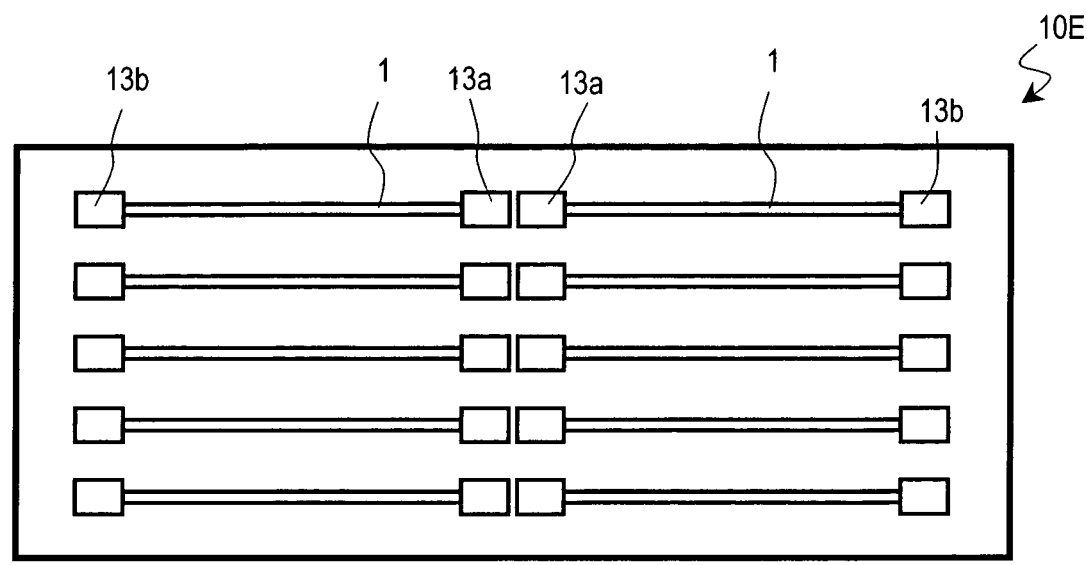
FIG. 20A and FIG. 20B are plan views schematically illustrating other illuminators 10E and 10F, respectively, according to a preferred embodiment of the present invention.
Figure 20B:
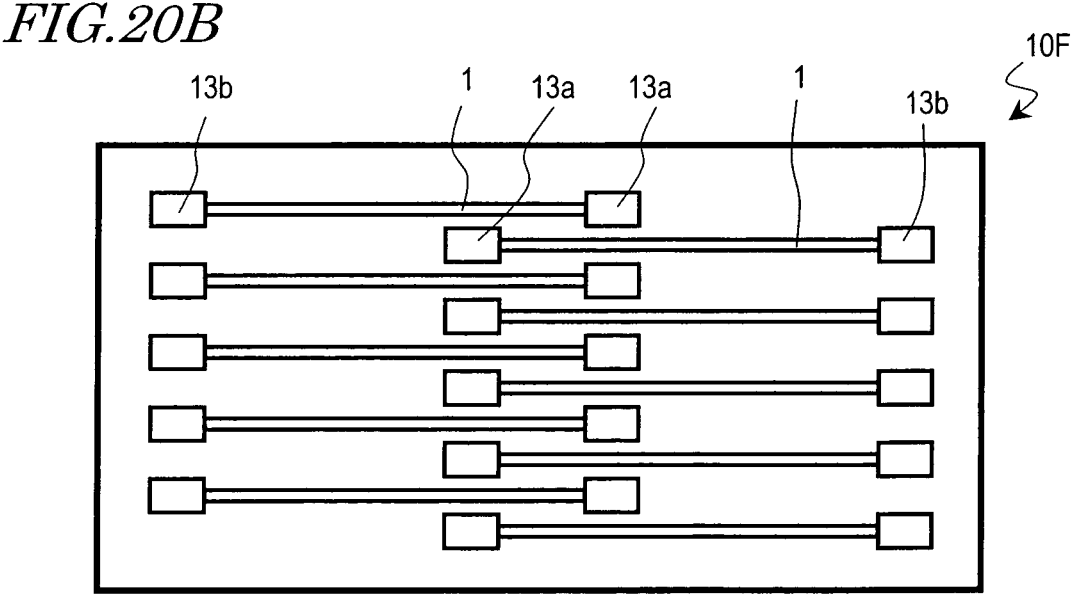

FIG. 20A and FIG. 20B illustrate other illuminators of other preferred embodiments of the present invention for which the optical material of the above-described preferred embodiments of the present invention can be used. Each of illuminators 10E and 10F illustrated in FIG. 20A and FIG. 20B includes a plurality of rod-shaped light sources 1.

While the rod-shaped light sources 1 are arranged in a single line in the illuminator 10C illustrated in FIG. 9, the rod-shaped light sources 1 are arranged in two lines in the illuminators 10E and 10F illustrated in FIG. 20A and FIG. 20B. With such an arrangement where the rod-shaped light sources 1 are arranged in a plurality of lines, short rod-shaped light sources can be used as the rod-shaped light sources 1. As compared with longer rod-shaped light sources, shorter rod-shaped light sources have a lower operating voltage, a better handling property and a better anti-shock property. Note that it is preferred that the rod-shaped light sources 1 all have the same length. If the rod-shaped light sources 1 all have the same length, the illuminator has little electrical and optical characteristics variations among different positions across the illuminator, and it is possible to easily control the light emission.

Each of the rod-shaped light sources 1 of the illuminators 10E and 10F is preferably held by a pair of holders 13a and 13b. If the holders 13a and 13b are made of an optical material as described above, it is possible to improve the reliability and the brightness. Particularly, if the inwardly-positioned holders 13a, which are located within the display area of the liquid crystal display device, are made of the optical material of preferred embodiments of the present invention, the brightness is improved significantly.

As described above, the present invention provides an optical material having a desirable heat-radiating property, an optical element made of such an optical material, and an illuminator and a display device including such an optical element.

The present invention can suitably be used as a diffusion plate, a lightguide or a light-scattering member for an illuminator.

While the present invention has been described with respect to preferred embodiments thereof, it will be apparent to those skilled in the art that the disclosed invention may be modified in numerous ways and may assume many embodiments other than those specifically set out and described above. Accordingly, it is intended by the appended claims to cover all modifications of the invention which fall within the true spirit and scope of the invention.

This non-provisional application claims priority under 35 USC §119(a) on Patent Applications No. 2003-421825 filed in Japan on Dec. 19, 2003 and No. 2004-323857 filed in Japan on Nov. 8, 2004, the entire contents of which are hereby incorporated by reference.

What is claimed is:

1. An optical material, comprising a resin having a luminous transmittance of about 70% or more, and a filler mixed therein having a thermal conductivity of about 3 W/m·K or more; wherein
the filler is made of diamond.

2. The optical material according to claim 1, wherein a thermal conductivity of the filler is about 10 W/m·K or more.

3. The optical material according to claim 1, wherein a luminous transmittance of the resin is about 80% or more.

4. The optical material according to claim 1, wherein the resin is polycarbonate.

5. The optical material according to claim 1, wherein a luminous transmittance of the resin is about 90% or more.

6. The optical material according to claim 1, wherein the resin is an acrylic resin.

7. The optical material according to claim 1, wherein the resin is polystyrene.

8. The optical material according to claim 1, wherein the resin is a methyl methacrylate-styrene copolymer resin.

9. The optical material according to claim 1, wherein the filler is particulate.

10. The optical material according to claim 9, wherein an average particle diameter of the filler is about 1 μm or more.

11. The optical material according to claim 1, wherein a refractive index of the resin is different from that of the filler so as to provide a light-diffusing property.

12. An optical element, comprising the optical material according to claim 1.

13. A diffusion plate, comprising the optical material according to claim 1.

14. The diffusion plate according to claim 13, wherein a haze value thereof is about 95% or more.

15. An illuminator, comprising a light source, and the diffusion plate according to claim 13 arranged to diffuse light output from the light source.

16. A display device, comprising the illuminator according to claim 15, and a display panel arranged to display an image by using light output from the illuminator.

17. A lightguide, comprising an optical material; wherein
the optical material includes a resin having a luminous transmittance of about 70% or more, and a filler mixed therein having a thermal conductivity of about 3 W/m·K or more; wherein
the filler has a particle diameter of less than about 100 nm.

18. An illuminator, comprising a light source, and the lightguide according to claim 17 arranged to guide light output from the light source in a predetermined direction.

19. A display device, comprising the illuminator according to claim 18, and a display panel arranged to display an image by using light output from the illuminator.

20. A light-scattering member for scattering light, comprising the optical material according to claim 1.

21. An illuminator for a display device provided on a back side of a display panel, comprising:
a plurality of rod-shaped light sources disposed generally parallel to one another; and a light-scattering member arranged to scatter light, including an optical material and disposed between two adjacent ones of the plurality of rod-shaped light; wherein the optical material includes a resin having a luminous transmittance of about 70% or more, and a filler mixed therein having a thermal conductivity of about 3 W/m·K or more.

22. A display device, comprising the illuminator according to claim 21, and a display panel arranged to display an image by using light output from the illuminator.

23. An illuminator for a display device provided on a back side of a display panel, comprising:
  at least one light source including a plurality of rod-shaped portions disposed generally parallel to one another, and a bent portion connecting two adjacent ones of the plurality of rod-shaped portions to each other; and
  a light-scattering member arranged to scatter light, including an optical material and disposed between two adjacent ones of the plurality of rod-shaped portions; wherein
  the optical material includes a resin having a luminous transmittance of about 70% or more, and a filler mixed therein having a thermal conductivity of about 3 W/m·K or more.

24. A display device, comprising the illuminator according to claim 23, and a display panel for displaying an image by using light output from the illuminator.

25. A light source holder for an illuminator, comprising an optical material; wherein
  the optical material includes a resin having a luminous transmittance of about 70% or more, and a filler mixed therein having a thermal conductivity of about 3 W/m·K or more.

26. An illuminator, comprising a light source and the light source holder according to claim 25 arranged to hold the light source.

27. A display device, comprising the illuminator according to claim 26, and a display panel arranged to display an image by using light output from the illuminator.

* * * * *

UNITED STATES PATENT AND TRADEMARK OFFICE
CERTIFICATE OF CORRECTION

PATENT NO.       : 7,309,143 B2
APPLICATION NO.  : 11/012738
DATED            : December 18, 2007
INVENTOR(S)      : Yoshiki Takata It is certified that error appears in the above-identified patent and that said Letters Patent is hereby corrected as shown below:

On the title page item [73], in the Assignee, "Kyoto" should be corrected to --Osaka--

(73) Assignee: Sharp Kabushiki Kaisha. ~~Kyoto~~ Osaka (JP)

Signed and Sealed this

Thirtieth Day of June, 2009

JOHN DOLL
*Acting Director of the United States Patent and Trademark Office*